US011221295B2

(12) United States Patent
Carty et al.

(10) Patent No.: US 11,221,295 B2
(45) Date of Patent: Jan. 11, 2022

(54) GAS PHASE FLUORESCENCE ANALYSIS

(71) Applicant: UNIVERSITY OF DURHAM, Durham (GB)

(72) Inventors: David Carty, Durham (GB); Eckart Wrede, Durham (GB); Nils Hendrik Nahler, Midlothian (GB)

(73) Assignee: UNIVERSITY OF DURHAM, Durham (GB)

( * ) Notice: Subject to any disclaimer, the term of this patent is extended or adjusted under 35 U.S.C. 154(b) by 951 days.

(21) Appl. No.: 15/748,508

(22) PCT Filed: Aug. 2, 2016

(86) PCT No.: PCT/EP2016/068471
§ 371 (c)(1),
(2) Date: Jan. 29, 2018

(87) PCT Pub. No.: WO2017/021424
PCT Pub. Date: Feb. 9, 2017

(65) Prior Publication Data
US 2018/0246036 A1 Aug. 30, 2018

(30) Foreign Application Priority Data
Aug. 3, 2015 (GB) .................................... 1513700

(51) Int. Cl.
*G01N 21/64* (2006.01)
*G01J 3/44* (2006.01)
(Continued)

(52) U.S. Cl.
CPC ....... *G01N 21/6402* (2013.01); *A61B 5/0071* (2013.01); *A61B 5/0075* (2013.01);
(Continued)

(58) Field of Classification Search
CPC .. G01N 21/6402; G01N 21/31; G01N 21/645; G01N 33/497; G01N 2201/06113;
(Continued)

(56) References Cited

U.S. PATENT DOCUMENTS

| 7,101,340 B1 | 9/2006 | Braun | |
| 2004/0162500 A1* | 8/2004 | Kline | A61B 5/412 600/532 |

(Continued)

FOREIGN PATENT DOCUMENTS

| WO | WO 2014/132077 | 9/2014 |
| WO | PCT/EP2016/068471 | 2/2017 |
| WO | WO 2017/021424 | 2/2017 |

OTHER PUBLICATIONS

Wang et al., "Breath acetone analysis of diabetic dogs using a cavity ringdown breath analyzer," 2014, IEEE Sensors Journal, vol. 14, No. 4, pp. 1117-1123. (Year: 2014).*

(Continued)

*Primary Examiner* — Kiho Kim
(74) *Attorney, Agent, or Firm* — Brian S. Boyer; Syndicated Law, PC

(57) ABSTRACT

Apparatuses and methods are provided for quantifying an analyte in a gas or liquid phase. A light source with an emission spectrum overlapping an absorption of the analyte, and a pair of reflective mirrors located on an optical axis to form an optical cavity can be included. An off-axis photon detector can be configured as a fluorescence detector and located off the cavity axis and arranged to provide a first signal in response to fluorescence within the cavity. An axial photon detector can be located axially, and external, to the cavity and arranged to provide a second signal. The portion of the apparatus including the light source, the cavity, and the axial photon detector can be configured with a cavity-enhanced absorption spectrometer, and the portion of the (Continued)

apparatus including the off-axis photon detector can be configured with a cavity-enhanced laser-induced fluorescence (CELIF) spectrophotometer.

23 Claims, 3 Drawing Sheets

(51) Int. Cl.
*G01N 33/497* (2006.01)
*A61B 5/08* (2006.01)
*G01N 21/31* (2006.01)
*A61B 5/097* (2006.01)
*A61B 5/00* (2006.01)
*G01N 33/00* (2006.01)

(52) U.S. Cl.
CPC .............. *A61B 5/082* (2013.01); *A61B 5/097* (2013.01); *G01J 3/4406* (2013.01); *G01N 21/31* (2013.01); *G01N 21/645* (2013.01); *G01N 33/497* (2013.01); *G01N 33/0057* (2013.01); *G01N 2201/06113* (2013.01)

(58) Field of Classification Search
CPC .............. G01N 33/0057; G01N 21/39; G01N 2021/391; A61B 5/0071; A61B 5/0075; A61B 5/097; A61B 5/082; G01J 3/4406
See application file for complete search history.

(56) References Cited

U.S. PATENT DOCUMENTS

| 2007/0229818 | A1 | 10/2007 | Duan et al. | |
| 2008/0179530 | A1* | 7/2008 | Liu | G01N 21/39 |
| | | | | 250/343 |
| 2009/0180119 | A1 | 7/2009 | Reeve et al. | |
| 2015/0131094 | A1* | 5/2015 | Alquaity | G01N 21/39 |
| | | | | 356/326 |

OTHER PUBLICATIONS

Blaikie, T.P., et al. Comparison of breath gases, including acetone, with blood glucose and blood ketones in children and adolescents with type 1 diabetes. J. Breath Res. 8(4) (2014).

Mizouri, A., Absolute density measurement of SD radicals in a supersonic jet at the quantum-noise-limit. Phys. Chem. Chem. Phys. 15:19575-19579 (2013).

Sanders, S. E., et al. Absolute absorption and fluorescence measurements over a dynamic range of 1016 with cavity-enhanced laser-induced florescence. arXiv:1308.1989v2 [physics.chem-ph] (2013).

Righettoni, M., et al. Monitoring breath markers under controlled conditions. J. Breath. Res. 9(4) (2015).

Wang, C. et al. A Study on Breath Acetone in Diabetic Patients Using a Cavity Ringdown Breath Analyzer: Exploring Correlations of Breath Acetone With Blood Glucose and Glycohemoglobin A1C. IEEE Sensors Jornal. 10(1): 54-63 (2010).

Anderson, J.C. Measuring Breath Acetone for Monitoring Fat Loss: Review. The Obesity Society (TOS). 23(12): 2327-2334 (2015) doi:10.1002/oby.21242.

\* cited by examiner

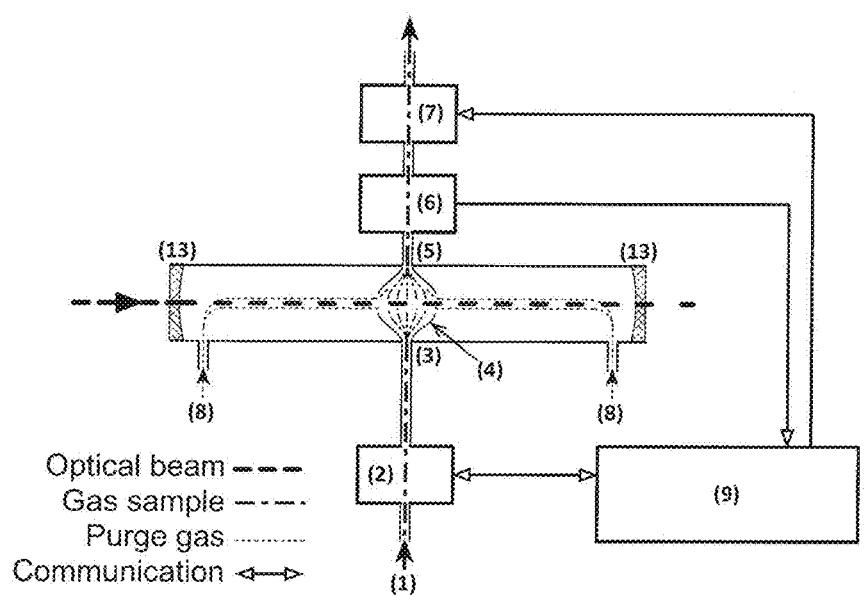
Figure 1a - gas handling and flows

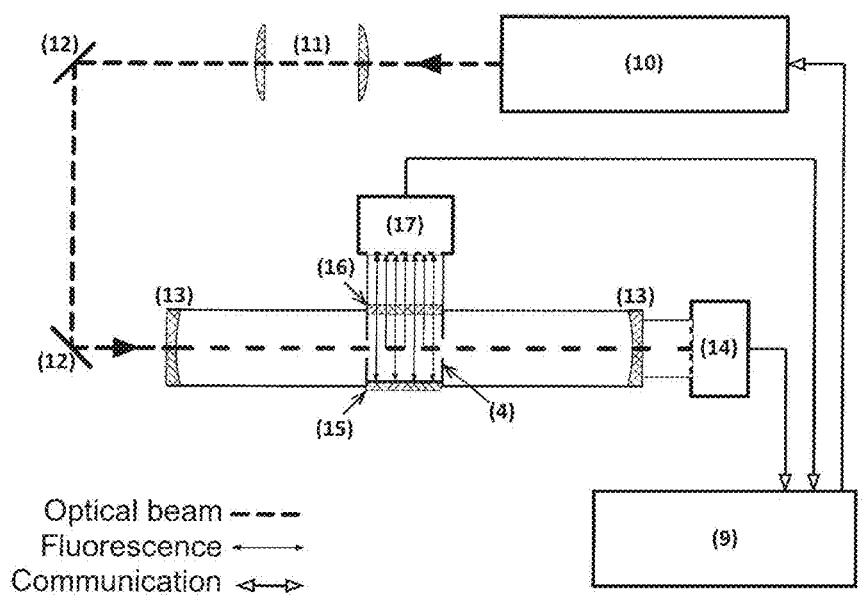
Figure 1b - optical setup

GAS PHASE FLUORESCENCE ANALYSIS

CROSS-REFERENCE TO RELATED APPLICATIONS

This application is a National Stage of International Application No. PCT/EP2016/068471, filed Aug. 2, 2016, which claims the benefit of GB 1513700.3, filed Aug. 3, 2015, each of which is incorporated herein by reference in its entirety.

BACKGROUND

Field of the Invention

This invention relates to a method and apparatus for quantifying a fluorescent analyte in a gas-phase sample, particularly but not exclusively for determination of a metabolite in exhaled breath.

A particular embodiment of the invention relates to measurement of the concentration of acetone in human or other mammalian exhaled breath. A further embodiment of this invention relates to detection and quantification of explosive materials which do not contain nitro groups, for example peroxide-based explosives.

Description of the Related Art

Diabetes mellitus is a group of metabolic diseases where defects in insulin action and/or secretion results in harmfully high blood glucose (BG) levels. Effective diabetes management can greatly reduce the risk of complications. However when poorly managed the disease can cause serious complications such as cardiovascular disease, kidney disease, blindness, amputation, diabetic ketoacidosis (DKA), depression, neuropathy and sexual dysfunction. Around 366 million people worldwide had diabetes in 2011. In the UK, 2.9 million people have been diagnosed with diabetes and it has been estimated that a further 850,000 are sufferers of the condition but have yet to be diagnosed. Including children, 15% have the non-preventable type I form (T1D), characterised by a lack of insulin production and the remaining fraction have the preventable type II form (T2D), which is linked with obesity and lifestyle. Children with diabetes have the worst rates of very high risk glucose control. In 2009/10, 9% of children with diabetes experienced at least one episode of acute DKA, a fast-developing and life-threatening emergency. DKA is caused by the build-up of body ketones, which are produced when the body burns fat instead of glucose. Some people with undiagnosed T1D do not receive a diagnosis until they are seriously ill with DKA.

DKA kills more than ten young people with T1D each year in the UK. The severity of DKA at diagnosis is inversely related to neurocognitive outcome leading to substantial subsequent health costs. Timely diagnosis is essential, yet primary and secondary healthcare teams frequently miss T1D/DKA diagnosis. The proportion of cases presenting DKA has not changed for many years despite intervention programmes, which reflects the difficulty in obtaining blood or urine samples. Hospital-based insulin treatment of DKA (in both children and in adults) uses measurement of blood pH and measurement of the blood ketone β-hydroxybutyrate to monitor response, but this is often problematic and inadequate—sampling can be difficult and the results of ketone measurement can be inaccurate, samples may need to be sent to a different location for analysis leading to untimely reporting of results and blood pH may remain low due to emerging hypochloraemia caused by saline treatment thus masking the response to treatment being measured.

Ketoacidosis can also be caused by starvation as a result of dieting or illness. The symptoms of ketoacidosis can appear in children, even in those that do not have T1D, and are often mistaken for food poisoning, which can lead to delays in appropriate treatment. Pregnant women with T1D during labour are susceptible to DKA brought on by the medical stress they are in. People with severe epilepsy can be treated with a ketogenic diet, which is effective only if the person remains ketotic thus making the diet extremely difficult to deliver and maintain safely.

A non-invasive method for diagnosis and monitoring of T1D/DKA as an alternative to blood analysis is the measurement of the concentration of the diabetes biomarker acetone in exhaled breath (Ref: T. P. J. Blaikie, et al., J. Breath Res., 8 (2014) 046010). Sensitive quantification of the very low concentrations of breath acetone is difficult. The presence of other gases in breath, including acetoacetate and 3-β-hydroxybutyrate, which are also associated with diabetes, as well as high concentrations of $H_2O$, $CO_2$, $N_2$ and $O_2$ means that high selectivity is required. For an acetone measurement device to be effective in a point-of-care (POC) setting, it should be portable outside a laboratory environment, affordable and offer a real-time on-line measurement reported directly and continuously from the patient. Such a device would thus remove any uncertainty a clinician may have and can ensure that treatment decisions are applied with confidence.

A large number of techniques for laser spectroscopic breath analysis have been used. These are reviewed in Wang, C.; Sahay, P. *Breath analysis using laser spectroscopic techniques: Breath biomarkers, spectral fingerprints, and detection limits*, Sensors 2009, 9, 8230-8262.

In order to compare techniques, individual techniques must weigh up against five criteria, all of which would be ideally satisfied: sensitivity, i.e. can an acceptably small change in analyte concentration be detected; selectivity—does the detection measure the target analyte without significant interference from other chemical species; POC—is the device portable enough to reside next to the patient; real time—can the correct measurement be made and results given back without an unacceptable delay; and online—can the sample go directly from the patient into the device. Table 1 summarises the criteria that can be met by the techniques that have been used for the measurement of acetone in breath.

TABLE 1

Summary of whether a particular technique meets criteria to an effective point-of-care device.

| Technique | Sensitivity | Selectivity | POC | Real time | Online |
|---|---|---|---|---|---|
| SPME-GC-MS | ✓ | ✓ | X | X | X |
| PTR-MS/SIFT-MS | ✓ | ✓ | X | ✓ | ✓ |
| Electrochemical | ✓ | X | ✓ | X | X |
| Si:WO₃ sensor | X | X | ✓ | ✓ | ✓ |
| CEAS | X | ✓ | ✓ | X | X |
| CRDS | X | ✓ | ✓ | ✓ | ✓ |

TABLE 1-continued

Summary of whether a particular technique meets criteria to an effective point-of- care device.

| Technique | Sensitivity | Selectivity | POC | Real time | Online |
|---|---|---|---|---|---|
| ICOS | ✓ | ✓ | ✓ | X | ✓ |
| CELIF | ✓ | ✓ | ✓ | ✓ | ✓ |

SPME-GC-MS, solid-phase micro-extraction mass-spectrometry;
PTR-MS, proton-transfer-reaction mass spectrometry;
SIFT-MS, selected-ion flow-tube mass spectrometry;
Si:WO₃ sensor, chemo-resistive sensor using Si-doped tungsten trioxide nanoparticles;
CEAS, cavity-enhanced absorption spectroscopy;
CRDS, cavity ring-down spectroscopy;
ICOS, integrated cavity-output spectroscopy and
CELIF, cavity-enhanced laser-induced fluorescence.

Gas chromatography (GC) has been used in breath analysis. This is used to isolate a particular breath analyte, such as acetone, where it is then detected—typically by mass spectrometry (MS). While this technique easily reaches the required sensitivity and selectivity, the instrumentation is prohibitively expensive for POC use. Real-time, on-line analysis is impossible because breath samples must be pre-concentrated using a technique such as solid-phase micro-extraction (SPME). Other MS techniques such as proton-transfer-reaction MS (PTR-MS) and selected-ion flow-tube MS (SIFT-MS) are better, but the instrumentation is not suitable for POC use on the grounds of size and cost. Electrochemical devices, such as a multi-wall carbon-nanotube/$SnO_2$ sensor, can be sensitive enough and may be good for POC use by virtue of being inexpensive and portable, but they do not meet any of the other criteria. The recent Si:$WO_3$ chemo-resistive sensor [M. Righettoni et al., *Monitoring breath markers under controlled conditions, J. Breath Res.*, 2015, 9, 047101], shows good correlation with PTR-TOF-MS over a limited dynamic range and requires specific breathing protocols. The laser-spectroscopy-based techniques cavity-enhanced absorption spectroscopy (CEAS), cavity ring-down spectroscopy (CRDS) and integrated cavity-output spectroscopy (ICOS) that have been used in acetone breath analysis have proved to be more promising. CEAS lacks sensitivity and the measurement must be done offline and not in real time using a sample bag that is taken to the device. CRDS only lacks sensitivity and ICOS only lacks the ability to obtain a measurement fast enough for real time results. Cavity-enhanced laser-induced fluorescence (CELIF) meets all desired criteria.

Cavity ring-down spectroscopy (CRDS) measures the absorption of light by the sample. CRDS is implemented by injecting a laser pulse into a stable optical cavity consisting of two highly reflective mirrors. When a laser pulse is incident on the back side of the first mirror, the majority of the pulse is reflected away from the cavity. However, a small portion of the pulse dependent on the finite reflectivity of the mirror, is injected into the optical cavity. When this injected pulse encounters the second highly reflective mirror, the majority of the remaining pulse is reflected back into the cavity while a minor fraction is transmitted and leaves the cavity. The laser pulse reflects back and forth between the mirror surfaces transmitting a small percentage of its intensity with each mirror encounter. The transmitted intensity usually follows an exponential decay and is monitored by a photodetector located behind the second mirror. With an "empty" cavity, i.e. without an absorbing species in the cavity (vacuum, sample without analyte or laser detuned from any absorption line), the time constant of the decay, called the ring-down time (RDT), is a measure of the reflectivity of the mirrors. Following introduction of an absorbing analyte species or tuning the laser onto an absorption line of a species in the cavity, the absorption increases leading to a faster decay and a shorter ring-down time. The decrease in the ring-down time depends on the absorption strength (absorption cross section) of the species, the particular wavelength and also the concentration of the species in the cavity. The concentration for the analyte is determined from the reduction in the ring-down time compared to the "empty" cavity and literature values for the absorption strength of the analyte. CRDS is able to determine absolute concentrations.

Laser-induced fluorescence (LIF) is an indirect detection technique. When an analyte molecule absorbs light it is excited into a higher energy state. This excited molecule can release its energy by emitting light (fluorescence) that is detected by a photodetector at an angle to the laser beam. However, other processes can prevent fluorescent light being emitted, hence, fluorescence by the molecule is a requirement. The amount of light detected depends on the intensity and wavelength of the incident laser light, the analyte concentration, the absorption strength of the analyte, the fraction of light emitted with respect to the light absorbed (fluorescence quantum yield of the analyte) and the efficiency of the LIF detection system. In general, only relative concentrations (e.g. when comparing two samples under otherwise identical conditions) can be determined via LIF. In order to determine the absolute analyte concentrations from the intensity of the detected fluorescence a complex and protracted calibration of the detection system is required.

SUMMARY OF THE INVENTION

The present invention uses CELIF which is a direct combination of the well-established and powerful laser-spectroscopic techniques cavity ring-down spectroscopy and laser-induced fluorescence.

According to a first aspect of the present invention, apparatus for quantifying an analyte in a gas or liquid phase sample comprises:

a light source with an emission spectrum that overlaps with an absorption of the analyte, a pair of reflective mirrors located on an optical axis to form an optical cavity, the cavity having a sample inlet and a sample outlet;

a fluorescence detector located at a location not on the cavity axis and arranged to provide a first signal in response to fluorescence within the cavity;

a photon detector located axially external to the cavity and arranged to provide a second signal;

wherein the apparatus including the light source, the cavity and the axial photon detector comprises a cavity-enhanced absorption spectrometer;

wherein the apparatus including the off-axis photon detector is configured to comprise a cavity-enhanced laser-induced fluorescence (CELIF) spectrophotometer;

means for supplying a pure gas sample or an analyte-containing gas sample to the cavity through the inlet;

a processor adapted to receive a first signal from the non axial photon detector and a second signal from the axial photon detector, and further adapted to provide a measurement of the analyte concentration in the sample.

According to a second aspect of the present invention, a method of quantifying an analyte in a gas phase sample comprises the steps of:

providing apparatus in accordance with the first aspect of the invention;

introducing an analyte-free gas sample into the cavity obtaining a background signal;

introducing a reference sample containing a quantity of the analyte into the cavity and obtaining a reference signal;

processing the background signal and reference signal to obtain an absolute absorption of the reference sample and to provide a calibration signal of the CELIF spectrophotometer;

introducing a specimen gas sample containing the analyte into the cavity obtaining a specimen signal;

processing the specimen signal and the calibration signal to obtain a measurement of the absolute concentration of the analyte in the specimen sample.

The method has the advantage of avoiding a need for external calibration.

The analyte has to be a fluorescent molecule, the light source being selected to irradiate the cavity at an absorption band for the analyte.

The analyte concentration, particularly a gaseous analyte may be measured repeatedly over time intervals of 100 ns to 5 ms.

The average value for the analyte concentration, particularly for a gaseous analyte, especially in a tidal breath sample, may be measured over a period of 1.0 ms to 0.03 s.

BRIEF DESCRIPTION OF THE FIGURES

The invention is further described by means of example but not in any limitative sense with reference to the drawings of which:

FIGS. 1a and 1b are schematic diagrams of apparatus in accordance with this invention.

DETAILED DESCRIPTION

Figure 2:
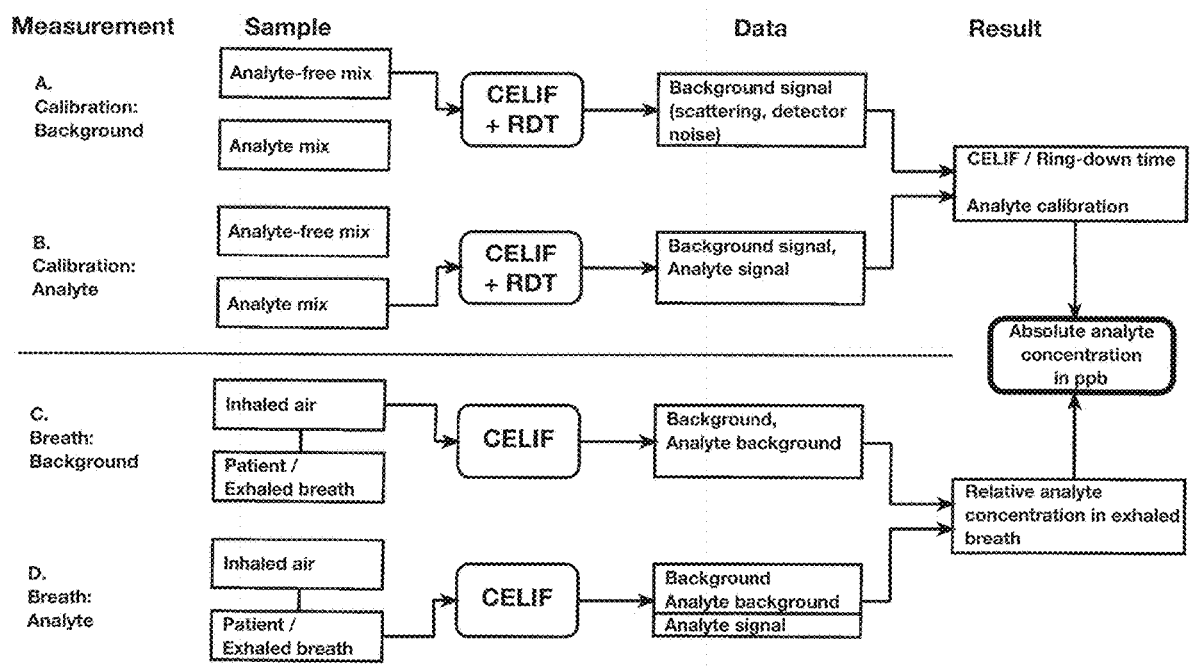
FIG. 2 is a flow chart illustrating the steps and measurement of acetone in exhaled breath.

The CELIF technique as described above, based on use of a pulsed laser as the light source and CRDS, can be implemented with any cavity-enhanced absorption spectroscopy (CEAS) method. A preferred embodiment uses CRDS.

Cavity-enhanced laser-induced fluorescence (CELIF) combines both the LIF and CRDS techniques in a single setup, using the same laser beam and detecting the same analyte molecules. The LIF aspect is used to detect the analyte. The optical cavity of the CRDS aspect very effectively eliminates stray light—a significant problem in traditional LIF implementations. The CRDS aspect is also used to correct the LIF for fluctuations of the intensity of the laser pulses (normalisation) and to provide the absolute calibration of the LIF detection system. At high concentrations, the reduction of the ring-down time (via CRDS measurement) yields an absolute measure of the analyte concentration which directly calibrates the intensity of the simultaneously measured fluorescence by the LIF detection system. The limit of detection (LOD) of the CRDS technique is reached when the ring-down time become indistinguishable from the ring-down time of a sample without analyte. Generally, the LOD of LIF is much lower compared to CRDS, and due to the cross calibration, much lower absolute concentration can be detected via CELIF. The LOD of CELIF is defined by the LIF background signal (without analyte) due to remaining stray and scattered light and the electronic noise of the detection system. CELIF is able to determine absolute concentrations well below the LOD of CRDS.

The basic requirements are as follows: (i) the CEAS delivers an absolute concentration for calibration; (ii) the CEAS aspect measures the amount of light present in the cavity for normalisation; (iii) the spectral output of the light source used in the CEAS aspect overlaps with a fluorescent excitation of the analyte.

Variants of CEAS may use different light sources. These light sources may be coherent or incoherent, pulsed, modulated or continuous, narrow- or broadband. Variants of CEAS use appropriate photodetectors. These photodetectors may be wavelength integrating, selective or dispersive.

In preferred embodiments the analyte is a gas phase analyte. The cavity may have an inlet and an outlet for the analyte sample.

The processor may be further adapted to calibrate the apparatus.

In a first embodiment a cell is located within the cavity.

In a second embodiment the cell comprises the cavity.

The fluorescence detector may be located in spaced relation to the cavity axis, preferably perpendicular to the axis.

Preferably the first and second signals are measured simultaneously. This serves to avoid any risk of change of the analyte concentration in a sample; and compensate for changes in the light intensity.

In a preferred embodiment the light source, the cavity and the axial photon detector comprise a cavity ring-down spectrometer.

The light source can be coherent for example a laser, or incoherent (e.g. a light-emitting diode, LED), pulsed or modulated or continuous, and narrowband (e.g. a laser) or broadband (e.g. an LED or a Xenon-arc lamp). The cavity mirrors should be matched to the light source (and the absorption band) with a typically reflectivity better than 99.8%.

In a preferred embodiment for use with a gaseous sample the optical cavity includes a region forming a cell (or a flow body, hereafter referred to as "cell") configured to contain the gas sample in the vicinity of the fluorescence detector so that fluorescence of an analyte within the cell is detected by the detector.

The cell may comprise the fluorescence detector located on a first side of the cell and a reflector on the opposite side remote from the detector and arranged to reflect light towards the detector, and axial apertures for passage of the laser beam through the cell. In a preferred embodiment the axis of the fluorescence detection (detector and reflector) is arranged perpendicular to the axis of the optical cavity with the gas inlet and outlet of the cell arranged perpendicular to both these axes. Alternatively, the apertures for the light beam could serve as gas in- and outlets or the gas inlet may be conveniently located in the reflector.

A supply of analyte-free purging gas may be provided adjacent the apertures. In a preferred embodiment the supply of purging gas may be arranged so that there is a flow of the purging gas from an inlet in an axial direction in the cavity towards an outlet, the outlet being located adjacent the cell so that the flow of purging gas is axially along the cavity towards the cell in use. Such an arrangement has an advantage that pressure of the purging gas maintains the analyte sample in the cell for a longer period and keeps the mirrors and surfaces that are not part of the cell analyte free.

Analytes may be selected from the group consisting of fluorescent molecules. Gaseous Acetone is a preferred analyte. Alternative preferred analytes are formaldehyde, which may be indicative of breast cancer, and HCN, which may be indicative of a *Pseudomonas aeruginosa* bacterial infection that is particularly problematic to sufferers of cystic fibrosis.

In the preferred embodiment the light source the beam shaping and steering optics, the cavity, the axial and non axial photon detectors and the fluorescence collection optics, together with the data acquisition form a cavity-enhanced laser-induced fluorescence (CELIF) spectrometer. An example is described in "Mizouri et al., *Phys. Chem. Chem. Phys.* 15, 19575 (2013) and Sanders et al., *arXiv:* 1308.1989v2 (2013)", the disclosure of which is introduced into this specification by reference for all purposes.

Gas containing the analyte may be introduced into and removed from of the cell by means of suitable input and output gas-handling units. A fraction of the light in the cavity is absorbed by the analyte, which subsequently emits fluorescence photons. The non axial photon detector, via the fluorescence collection optics, may detect within a predetermined time range (the "acquisition time") analyte-fluorescence photons (the "analyte signal") and a "background signal" consisting of photons from: Rayleigh scattering, fluorescence of mirror materials, surface scattering and extraneous sources. The "total signal" for each acquisition time, which is the sum of the analyte signal and the background signal, is recorded as number of detected photons, or integrated photon intensity. The total signal may be counted, or averaged over multiple acquisitions. A background signal is determined by performing a separate and identical measurement without the analyte. Both the total signal and the background signal may be normalised using the light intensities obtained from the axial photon detector integrated over the acquisition time. These are proportional to the light intensities inside the cavity. The analyte signal may be obtained by subtracting the normalised background signal from the normalised total signal.

In a preferred embodiment the CEAS method comprises use of narrowband pulsed laser cavity ring-down spectroscopy (CRDS). Light from a short-pulse, high repetition rate Nd:YAG laser (typically specifications for acetone detection: 266 nm, 15 kHz repititon rate, <3 ns pulse length, up to 100 mW output power) is passed through beam-shaping optics to match the laser-beam profile to the cavity. The axial detector is typically a photo-multiplier tube (PMT) or a photo diode with sufficient gain and time resolution to determine the ring-down time.

The analyte signal is converted into an analyte concentration using a separate calibration measurement obtained by cavity ring-down spectroscopy (CRDS). The cavity is first filled to a known pressure with a premixed gas mixture containing the analyte and a ring-down time is obtained from the ring-down transient by means of a regression analysis. The cavity is flushed and then filled to the same pressure as above with an analyte-free gas mixture and a ring-down time obtained. The analyte concentration is obtained in the usual way provided the appropriate absorption cross section of the analyte is known. For both measurements, the total signal from the off-axis photon detector is recorded simultaneously and a calibration factor obtained. The calibration factor can then be used to convert analyte signal into analyte concentration.

In another preferred embodiment incoherent broadband cavity-enhanced absorption spectroscopy (IBBCEAS) is used as the CEAS method. Light from a light-emitting diode (LED, typical specification for acetone detection: centre wavelength 250-300 nm, bandwidth 10 nm, up to 100 mW) may be spectrally narrowed by means of an optical filter or dispersive optics. The light may pass through beam-shaping optics to maximise the coupling of the light into the cavity. The axial detector is typically a solid-state CCD spectrometer with sub-nm spectral resolution that measures the light intensity exiting the cavity as a function of wavelength (the "cavity spectrum"). Spectrally integrated cavity spectra are used for the normalisation of the total and background fluorescence signals. Wavelength dependent mirror reflectivity is determined by a separate measurement as disclosed by G. Gagliardi, H.-P. Loock (eds.), *Cavity-Enhanced Spectroscopy and Sensing, Springer Series in Optical Sciences* 179, 2014.

The analyte signal may be converted into an analyte concentration using a separate calibration measurement. The cavity may be first filled to a known pressure with a premixed gas mixture containing the analyte and a first cavity spectrum is obtained. The cavity is then flushed and filled to the same pressure as above with an analyte-free gas mixture and a second cavity spectrum obtained. The first and second spectra may be combined with the wavelength dependent mirror reflectivity as disclosed by G. Gagliardi, H.-P. Loock (eds.), *Cavity-Enhanced Spectroscopy and Sensing, Springer Series in Optical Sciences* 179, 2014 in order to obtain the analyte concentration, provided the appropriate absorption cross section of the analyte is known. For both measurements of the cavity spectrum, the total signal from the off-axis photon detector is recorded simultaneously and a calibration factor obtained. The calibration factor can then be used to convert analyte signal into analyte concentration.

If the spectral composition of the light source is known and can be controlled, for example using a narrowband filter or using a temperature stabilised LED, and the wavelength dependent mirror reflectivity is known, a wavelength integrating axial photon detector (e.g. PMT or photo diode) may be employed.

In another preferred embodiment, phase-shift cavity ring-down spectroscopy (PS-CRDS) may be used as the CEAS method. Light from a light-emitting diode (LED, typical specification for acetone detection: centre wavelength 250-300 nm, bandwidth 10 nm, up to 100 mW) may be spectrally narrowed by means of an optical filter or dispersive optics to typically 1 nm. The intensity if the light source may be modulated with typically 300 kHz. The light may pass through beam-shaping optics to maximise the coupling of the light into the cavity. The axial detector is typically a photo-multiplier tube (PMT) or photo diode with sufficient gain and time resolution to determine the modulation-response of the cavity. A processor may determine the phase-shift between the light entering and exiting the cavity and their modulation depth. The processor may also provide the ring-down time (i.e. the "cavity lifetime") and light intensity exiting the cavity as common in frequency-domain lifetime measurements. The ring-down time may be derived from the phase shift or the modulation depth. The light intensities may be used for the normalisation of the total and background fluorescence signals.

The analyte signal may be converted into an analyte concentration using a separate calibration measurement obtained by PS-CRDS. The cavity may be first filled to a known pressure with a premixed gas mixture containing the analyte and a ring-down time may be obtained. The cavity is then flushed and filled to the same pressure as above with an analyte-free gas mixture and a ring-down time may be obtained. The analyte concentration may be obtained in the usual way provided the appropriate absorption cross section of the analyte is known. For both measurements, the total signal from the off-axis photon detector may be recorded simultaneously and a calibration factor obtained. The calibration factor can then be used to convert an analyte signal into an analyte concentration.

When measuring analyte concentrations in exhaled breath an appropriate means of sampling the breath is employed, including, but not exclusively selected from: a nasal cannula, a facemask, a breathing tube, a sample bag, a buffered end tidal sampler or alveolar separation sampler, or an advantageous combination of these devices. In an advantageous embodiment, a CELIF spectrometer for breath analysis is coupled with a breath sampling method that allows for real-time measurement of the breath. In order to select the important end-tidal part of the breath, a sufficiently large number of concentration measurements must be made within that time to characterise the breath concentration profile, so that the peak (end-tidal) concentration can be identified and recorded. The precision of the measurements depends, on the characteristics of the light source, the analyte density being measured and the duration of a single breath (respiratory rate). It may be necessary, depending on the desired measurement precision, to average the end-tidal concentrations of multiple breaths.

The invention has particular benefit in that the concentration of acetone in different parts of exhaled breath can be observed in real time. This permits measurement to be made of the acetone present in a desired part of a breath profile, for example the end tidal, alveolar breath.

According to a further aspect of the present invention there is provided a method of detecting or monitoring a type 1 diabetes in a patient comprising the step of measuring acetone in exhaled breath using apparatus in accordance with the previous aspect of the present invention.

Apparatus of the present invention may be used for measurement of exhaled acetone in children and adults, for example in a hospital ward. The insulin-treatment regimen that produces an optimum acidosis resolution rate in a given individual is unknown and alterations in the rate of insulin administration beyond the first 6-8 hours of treatment are linked to 'persisting ketosis'. There will is inherent variability in insulin sensitivity that may reflect the nature and severity of the acute illness, the extent of the metabolic imbalance, patient physique and innate 'inherited' insulin sensitivity. The amount of insulin that will produce a desired rate of acidosis resolution can only be calculated and revised appropriately in the context of regular real-time feedback regarding patient response. Glucose and ketone concentrations are routinely measured in venous or capillary blood during treatment but glucose levels are not closely related to acid-base balance and bedside ketone testing is both intermittent and notoriously inaccurate at high ketone levels and when samples are obtained from poorly perfused tissue.

Apparatus of the present invention may also be used for monitoring children with intractable epilepsy. Such children may be treated with a high ketone diet. The ketone levels need to be maintained above the treatment threshold without reaching a sufficiently high level at which a child may become sick.

A further application of the present invention is for measurement of ketone levels in pregnant women who may develop ketoacidosis while giving birth or in other high stress situations such as while undergoing surgery. Furthermore the invention may also be used for monitoring children who develop ketoacidosis in situations in which they have not eaten for a period of 24 hours or longer, for example during a stomach upset.

A further advantageous aspect of this invention provides a method of use of apparatus in accordance with the first aspect of this invention for detection of acetone vapour released from an acetone containing explosive composition, particularly, for detection of a triacetone triperoxide (TATP) explosive composition.

TATP has been used in improvised explosive devices. The absence of nitro groups makes TATP explosives hard to detect by conventional means. However, TATP is made by reacting acetone with hydrogen peroxide. Unreacted acetone or degradation products can be detected by apparatus in accordance with the present invention, particularly at low concentrations.

FIGS. 1a and 1b are schematic diagrams of apparatus in accordance with this invention. The apparatus shown in FIGS. 1a and 1b comprises a gas inlet (1) which may comprise a face mask, nasal cannula or breathing tube with a hose connected to an air manifold (2) The air manifold (2) is connected to the inlet of the cavity (3). The air manifold may include a $CO_2$ monitor and/or a pressure sensor, main stream or side stream, operatively coupled to a control and data acquisition module (9). Gas from the manifold is drawn through an enclosed cell (4) with small openings on the optical axis. The cell (4) may comprise a flow body to shape the gas flow. A gas outlet (5) is connected to a flow meter (6) followed by a regulated fan or a regulated valve and pump (7). Two or more purge gas inlets (8) may have regulating valves and are connected to a supply of nitrogen or clean air. The analyte containing gas is maintained mostly inside the cell by passage of the purge gas from the inlets (8) axially towards the cell (4), in order to prevent contamination of the mirrors (13). A light source (10), which may include spectral filters and pulsing or modulation electronics, is connected to beam-shaping optics (11) arranged to match the output of the light source to the optical cavity (13). Beam-steering optics (12) align the light beam along the axis of the optical cavity formed by the mirrors (13). An axial photon detector (14), typically a photomultiplier tube, is arranged axially from the laser source behind mirror (13). Fluorescence-collection optics, which may include a mirror (15), and an optical filter (16) to suppress scattered incident light are coupled to a photon detector (17), typically a photon multiplier tube. The cavity axis, the axis of the fluorescence collection and the direction of the gas flow are typically mutually perpendicular. A multi-channel digitiser and microprocessor (9) serves to control the function of the apparatus and data acquisition.

Components (9-17): the laser; the beam shaping and steering optics; the cavity; the axial and off-axis photon detectors and the fluorescence collection optics, together with the data acquisition, form a cavity-enhanced laser-induced fluorescence (CELIF) spectrometer. An example of such a spectrometer is described in "Mizouri et al., *Phys. Chem. Chem. Phys.* 15, 19575 (2013) and Sanders et al., *arXiv:*1308.1989v2 (2013)", the disclosure of which is introduced into this specification by reference for all purposes.

FIG. 2 illustrates the steps taken to measure acetone in a patient's breath. Similar steps are taken to measure an alternative analyte.

A typical measurement of acetone in exhaled breath involves the steps of calibration, breath acetone measurement, data analysis. This may be followed by diagnosis and treatment intervention.

The calibration measurement may be carried out using a clean that is analyte-free air sample and a prepared analyte-air mixture. The clean sample is introduced into the cavity and is used to measure a reference ring-down time and the background scattering signal (measurement A of FIG. 2). The acetone-air mixture is sufficiently concentrated that a reduction in the ring-down time can be detected. The ring-down time measurement provides a value which quantifies the absolute amount of acetone in the acetone-air mixture. A parallel fluorescent measure (measurement B) then provides the absolute calibration of the fluorescent signal.

Prior to making breath measurements, the background scattering signal and fluorescence from background acetone in the air supplied to the patient is measured (measurement C) and subsequently subtracted from the exhaled breath measurement (measurement D). Measurements C and D provide the relative acetone concentration which, linked to the calibration (measurements A and B) yields the absolute acetone concentration in the analysed breath.

Air is supplied to a patient via a manifold, breathing mask or breathing tube. The concentration of acetone in the supplied air (measurement C) and in the exhaled breath from the patient (measurement D) are determined using CELIF instrument. During measurement C the air flow through the air manifold and the cell is maintained by the fan or pump. Valves in the air manifold ensure that measurement C does not contain any exhaled breath while measurement D only contains exhaled breath.

Measurement of the acetone concentration in exhaled breath with sufficient time resolution allows identification of the alveolar part of the expired breath. This allows an accurate measurement of acetone to be made during each expiration. The acetone concentration may be used as a measure of blood ketone concentration and blood pH.

The invention claimed is:

1. Apparatus for quantifying an analyte in a gas phase tidal breath sample comprising:
   a light source with an emission spectrum that overlaps with an absorption of the analyte, a pair of reflective mirrors located on an optical axis to form an optical cavity wherein the optical cavity includes a region forming a cell and the cell has a gas inlet and an outlet for the analyte sample;
   an off-axis photon detector configured as a fluorescence detector located at a location not on the cavity axis and arranged to provide a first signal in response to fluorescence within the cavity;
   an axial photon detector located axially external to the cavity and arranged to provide a second signal; and,
   a pump for supplying a pure sample or an analyte-containing sample to the cavity;
   wherein,
   the portion of the apparatus including the light source, the cavity, and the axial photon detector is configured to comprise a cavity-enhanced absorption spectrometer;
   the portion of the apparatus including the off-axis photon detector is configured to comprise a cavity-enhanced laser-induced fluorescence (CELIF) spectrophotometer; and,
   the cell comprises the fluorescence detector located on a first side of the cell and a reflector on the opposite side remote from the fluorescence detector and arranged to reflect light towards the detector, the cell further comprises axial apertures for passage of the laser beam through the cell, wherein the axis of the fluorescence detector and reflector is arranged on a different axis from the axis of the optical cavity, and the gas inlet and outlet of the cell are arranged on a different axis than both the axis of the optical cavity and the axis of the fluorescence detector and reflector.

2. Apparatus as claimed in claim 1, wherein the light source, the cavity and the axial photon detector comprise a cavity ring-down spectrometer.

3. Apparatus as claimed in claim 1, wherein the processor is adapted to calibrate the apparatus.

4. Apparatus as claimed in claim 1, wherein the analyte is a gas phase analyte.

5. Apparatus as claimed in claim 1, wherein the fluorescence detector is located in spaced relation to the cavity axis.

6. Apparatus as claimed in claim 1, arranged so that the first and second signals are measured simultaneously.

7. Apparatus as claimed in claim 1, wherein the analyte is a ketone or an aldehyde.

8. Apparatus as claimed in claim 1, wherein the analyte is gaseous acetone.

9. Apparatus as claimed in claim 1, wherein a concentration of the analyte is measured repeatedly over time intervals of 100 ns to 5 ms.

10. Apparatus as claimed in claim 1, applied to breath analysis wherein an average value for a concentration of the analyte is measured over a period from 1.0 ms to 0.03 s.

11. Apparatus for measuring acetone in exhaled breath further comprising:
    a breath connector connected to an inlet of apparatus as claimed in claim 1.

12. Apparatus for measuring acetone in exhaled breath as claimed in claim 11, wherein the breath collector comprises a manifold, face mask, or breathing tube.

13. A method of quantifying an analyte in a tidal breath sample comprising the steps of:
    providing apparatus as claimed in claim 1;
    introducing an analyte-free sample into the cavity obtaining a background signal;
    introducing a reference sample containing a quantity of the analyte into the cavity and obtaining a reference signal;
    processing the background signal and reference signal to obtain an absolute absorption of the reference sample and to provide a calibration signal for the CELIF spectrophotometer;
    introducing a specimen sample from the tidal breath containing the analyte into the cell obtaining a specimen signal; and,
    processing the specimen signal and the calibration signal to obtain a measurement of the absolute concentration of the analyte in the specimen gas sample from the tidal breath.

14. A method as claimed in claim 13, wherein the analyte is a ketone or an aldehyde.

15. A method as claimed in claim 13, wherein the analyte is gaseous acetone.

16. A method for measuring acetone in exhaled breath as claimed in claim 15 wherein the breath collector comprises a manifold, face mask, or breathing tube.

17. A method as claimed in claim 13, wherein the analyte concentration is measured repeatedly over time intervals of 100 ns to 5 ms.

18. A method as claimed in claim 13, applied to breath analysis wherein an average value for the analyte concentration is measured over a period from 1.0 ms to 0.03 s.

19. A method as claimed in claim 13, wherein the obtaining of the background signal, the obtaining of the reference signal, and the obtaining of the reference signal include simultaneously measuring the first signal from the off-axis photon detector and the second signal from the axial photon detector.

20. A method for measuring acetone in exhaled breath comprising:
    a breath connector connected to an inlet of apparatus as claimed in claim 1.

21. A method of using the apparatus as claimed in claim 1 for detection of an explosive composition, the method comprising:
- providing apparatus as claimed in claim 1;
- introducing an analyte-free sample into the cavity obtaining a background signal, the analyte including the explosive composition;
- introducing a reference sample containing a quantity of the analyte into the cavity and obtaining a reference signal;
- processing the background signal and reference signal to obtain an absolute absorption of the reference sample and to provide a calibration signal for the CELIF spectrophotometer;
- introducing a specimen sample containing the analyte into the cell obtaining a specimen signal; and,
- processing the specimen signal and the calibration signal to obtain a measurement of the absolute concentration of the explosive composition in the specimen gas sample.

22. A method of detecting or monitoring Type 1 diabetes in a patient comprising the steps of:
- measuring acetone in exhaled breath from the patient using the apparatus as claimed in claim 1.

23. A method of detecting ketone acidosis in a patient comprising:
- measuring acetone in exhaled breath from the patient using the apparatus as claimed in claim 1.

* * * * *